United States Patent
Majewski et al.

(10) Patent No.: US 7,807,625 B2
(45) Date of Patent: Oct. 5, 2010

(54) ANTI-WRINKLE COMPOSITION

(75) Inventors: George P. Majewski, Redondo Beach, CA (US); Amit R. Shah, Commack, NY (US); John L. Gormley, Midland Park, NJ (US); Krzysztof Bojanowski, Santa Paula, CA (US)

(73) Assignee: Grant Industries, Inc, Elmwood Park, NJ (US)

( * ) Notice: Subject to any disclaimer, the term of this patent is extended or adjusted under 35 U.S.C. 154(b) by 682 days.

(21) Appl. No.: 11/654,406

(22) Filed: Jan. 17, 2007

(65) Prior Publication Data

US 2007/0166267 A1 Jul. 19, 2007

Related U.S. Application Data

(60) Provisional application No. 60/760,034, filed on Jan. 18, 2006.

(51) Int. Cl.
- *A01N 37/18* (2006.01)
- *A61K 38/00* (2006.01)
- *A61K 36/00* (2006.01)
- *A61K 8/02* (2006.01)
- *A61K 33/00* (2006.01)

(52) U.S. Cl. .......................... 514/2; 424/725; 424/401; 514/1

(58) Field of Classification Search .................. None
See application file for complete search history.

(56) References Cited

U.S. PATENT DOCUMENTS

| | | | |
|---|---|---|---|
| 4,814,173 A | 3/1989 | Song et al. | |
| 4,880,630 A | 11/1989 | Novak | |
| 5,902,591 A | 5/1999 | Herstein | |
| 6,194,452 B1 * | 2/2001 | Murad | 514/474 |
| 6,875,744 B2 | 4/2005 | Owen | |
| 6,974,799 B2 * | 12/2005 | Lintner | 514/18 |
| 2004/0147443 A1 * | 7/2004 | Renault | 514/12 |
| 2005/0148495 A1 | 7/2005 | Lambert, Jr. et al. | |

FOREIGN PATENT DOCUMENTS

JP 2002138045 A * 5/2002

OTHER PUBLICATIONS

Zhao et al. "Lycium barbarum glycoconjugates: effect on human skin and cultured dermal fibroblasts". Phytomedicine, vol. 12, No. 1-2 (2005):131-137, PubMed Abstract only..*

Phytomedicine 12 (2005) pp. 131-137; H. Zhao et al; www.sciencedirect.com; Lycium barbarum glycoconjugates: . . . .

* cited by examiner

*Primary Examiner*—Amy L Clark
(74) *Attorney, Agent, or Firm*—Jonathan Myers; Andrew Wilford

(57) ABSTRACT

A composition is disclosed for treating the skin comprising an acylated short chain bioactive peptide and *Lycium barbarum* extract product. Also disclosed is a method for topically administering the composition in an amount therapeutically effective to reduce wrinkles by building the dermal fibroblast matrix. The composition may contain dimethylisosorbide or ethoxydiglycol as solubilizing and penetration enhancers for the hydrophobically modified peptide.

4 Claims, No Drawings

ANTI-WRINKLE COMPOSITION

CROSS REFERENCE TO RELATED APPLICATION

This application is related to provisional application 60/760,034 filed 18 Jan. 2006.

FIELD OF THE INVENTION

The invention relates to a topical composition of acylated oligopeptide and *Lycium barbarum* extract product for treatment of fine lines and wrinkles in facial skin by improving fibroblast matrix and a method of using said composition. The invention further relates to a method of treating wrinkled skin by topically administering the composition to an individual in need of such treatment.

BACKGROUND OF THE INVENTION

U.S. Pat. No. 6,875,744 B2 discloses short bioactive peptides that are primarily made from phenylalanine, alanine, leucine and lysine. Such peptides are water soluble or miscible and have been reported to offer a low in-vitro minimum inhibitory concentration (MIC) against *P. acnes*. Benefits for hydrophobic acylated peptides of similar sequences have been reported and include increasing cell density of fibroblast-cells in the Cyquant cell proliferation assay (Molecular probes, C-7026) due to boosting the immune system by acting like a host defense peptide. Host defense peptides boost the innate immune system and have been shown to have a number of immunomodulatory functions including altering host gene expression, acting as chemokines and/or inducing chemokine production, inhibiting lipopolysaccharide induced pro-inflammatory cytokine production, promoting wound healing, and modulating the responses of dendritic cells and cells of the adaptive immune response. The boosting of such aspects of healthy skin are the same as are required for younger and less-wrinkled skin.

It is not generally recommended that such peptides be stored in solution. However, the shelf life of peptides is extended for sequences not containing Cysteine, Methionine, Tryptophan, Asparagine and Glutamine.

Peptides are not very useful if they are insoluble in the aqueous buffers required for testing in bioassay systems. Peptides can be made more lipophilic with long chain (C12-C22) alkyl esters or amides on the terminus to modify the interaction of the peptide with skin lipids but this modification drastically changes the solubility and makes peptides difficult to deliver in a stable aqueous cosmetic vehicle. Many biochemists use dimethylformamide or dimethylsulfoxide to help dissolve peptides for aqueous bioassay. Both of these solvents are not considered acceptable for cosmetic use. Solvents like ethoxydiglycol or dimethylisosorbide are useful cosmetic solvents for enhancing skin activity and can help solubilize the lipophilic peptide in an oil phase. However, formulations of excess lipophilic solvent can remove surface lipids and leave the skin feeling dry or brittle. U.S. Pat. No. 4,814,173 teaches the combination of dimethylisosorbide, peptide and silicone elastomers as part of a preferred transdermal matrix system.

Wolfberry extract, goji berry or *Lycium barbarum* extract are considered natural anti-aging foods of originally Chinese and Mongolian origin. U.S. Pat. No. 4,880,630 gives examples of how to extract *Lycium halimifolium* for use as an active ingredient, similar to methods used for *Lycium barbarum*. It was reported in Phytomedicine 12 (2005) 131-137 that *Lycium barbarum* glycoconjugates (LbGp), particularly LbGp5, had promoted the in-vitro survival of human fibroblasts in sub-optimal conditions. There still remains an unmet need for improved rebuilding of the in-vivo/ex-vivo skin matrix by synergistically improving dermal fibroblast regulation with ingredients delivered topically and that maintain the skin in a moist healthy state and maintain the proper skin barrier lipid balance.

OBJECTS OF THE INVENTION

It is an object of the invention to provide a cosmetic composition having the capability of rebuilding of the in-vivo/ex-vivo skin matrix by synergistically improving dermal fibroblast regulation with ingredients delivered topically.

It is a further object of the invention to provide a cosmetic composition that will maintain the skin in a moist healthy state and maintain the proper skin barrier lipid balance.

SUMMARY OF THE INVENTION

We have achieved the stated objects by providing a cosmetic composition comprised of:

0.001% to about 0.1% by weight percent of an oligopeptide of 3-20 amino acid units wherein the oligopeptide is acylated with a $C_2$ to $C_{22}$, preferably a $C_{12}$ to $C_{22}$ acyl group; and 0.01% to about 80% by weight of an extract of *Lycium barbarum*, in a cosmetically acceptable vehicle consisting of an emulsion, lotion, spray, aerosol, powder, ointment, cream and foam.

Preferably, the composition is an emulsion and the acylated oligopeptide peptide is dispersed or solubilized in the oil phase of the cosmetic emulsion and the aqueous portion contains the *Lycium barbarum* extract product. More preferably, the acylated oligopeptide peptide is first dissolved in ethoxydiglycol or dimethylisosorbide prior to adding it to the oil phase and combining it with other oil phase ingredients. About 0.2% to about 5% emulsifier is used to stabilize the emulsion.

According to a preferred feature of the invention, the oil-phase of the emulsion composition contains one or more of the following ingredients: 1.0 to about 20% by weight of an oil-absorbing silicone-elastomer crosspolymer gel and 0.1% to about 0.5% by weight of a retinoic acid ester.

In yet another preferred feature, the aqueous phase of the emulsion contains 0.01% to about 2% by weight of a non-comedogenic, hydrated film-forming graft copolymer formed from the solution polymerization of dimethylacrylamide, acrylic acid, polystyrene, and methacrylate monomers to maintain dermal contact of the peptide emulsion for extended intervals of time.

The preferred oligopeptides include those exhibiting dermal fibroblast matrix rebuilding properties. This sequence class is described in U.S. Pat. No. 6,875,744 B2 and the specific sequence most preferred herein is: Phe Ala Leu Leu Lys Leu (SEQ ID NO:1). The preferred acyl group used to acylate the oligopeptides is an alkanoyl group, and a preferred alkanoyl group is palmitoyl. The preferred palmitoyl oligopeptides are palmitoyl tripeptide, palmitoyl tetrapeptide, palmitoyl pentapeptide, palmitoyl hexapeptide, palmitoyl hexapeptide-3, and more preferably a palmitoyl hexapeptide with only the four amino acids phenylalanine, alanine, leucine and lysine in the sequence for increased solution stability, including palmitoyl hexapeptide-6; and still more preferably the sequence FALLKL-$NH_2$ modified with a palmitoyl group. The latter compound is commercially available from Helix Biomedix, Bothell, Wash. under the name HB168PAL.

The acyl group may acylate the N-terminal of the oligopeptide, one of the functional groups on a side chain of an amino acid within the oligopeptide, wherein the functional group is capable of acylation with an acyl group, especially a hydroxy, amino or carbamoyl functional group, or at the C-terminal of the oligopeptide, especially-when the C-terminal is amidated wherein the acyl group acylates the amido nitrogen of the amidated C-terminal.

Another preferred group of acylated oligopeptides includes oligopeptides whose N-terminal is acylated with a $C_2$ to $C_{22}$ acyl group, preferably alkanoyl. The most preferred acyl group is acetyl. A particular preferred compound within this group is commercially available under the name ARGIRELINE® from Lipotec, Barcelona, Spain. The oligopeptide has the following sequence:

Glu Glu Met Gln Arg Arg (SEQ ID No:2) and the structural formula for ARGIRELINE® is as follows:

Acetyl-Glu Glu Met Gln Arg Arg-$NH_2$.

*Lycium barbarum* is of the family Solanaceae (nightshade), with the common name of matrimony vine and synonyms *Lycium halimifolium* and *Lycium vulgare*. The fruit of *Lycium barbarum* is called Fructus Lycii, Chinese wolfberry, wolfberry or goji berry and it is the extract of the dried fruit that is generally used herein. Extracts of the plant bark may also be used herein, but the berry source is preferred and may be purchased as dried goji berries at a natural food market. The *Lycium* extract is a tea made by passing hot water through ground up berries. The extract is preferably filtered prior to use. This invention makes use of all such extracted berry products, from dilute liquid of 0.1% solids to 100% solid concentrate. Purified products from the wolfberry or goji berry extract may also be used as this extract contains at least 0.45 mg of standardized *Lycium barbarum* glucoconjugate complex LbGp per gram dried berry weight and is considered the main anti-cancer and anti-aging active in this plant family. This active principle has shown selective regulation of matrix metalloproteinase MMP-1 expression. One glycoconjugate, LbGp5 is an efficient antioxidant and allows cells to maintain regular metabolic functions in suboptimal conditions. Preferred is the purified LbGp (the blend of *Lycium barbarum* glycoconjugates 1-5), more preferred is the single glycoconjugate LbGp-5.

As will be described more fully, the combination of the acylated oligopeptide and *Lycium barbarum* extract was unexpectedly found to be synergistic towards improving the fibroblast matrix.

The acylated oligopeptide is preferably first solubilized in dimethylisosorbide (Arlasolve DMI—Uniqema, New Castle Del.) or ethoxydiglycol (Transcutol CG—Gattefosse USA, Paramus N.J.) prior to forming the final oil phase of the emulsion.

The emulsifier is required for making a stable emulsion and may be included in both the water and oil phases of the emulsion to best match the requirements of a formula. Surfactant emulsifiers may include, but are not limited to: halide or amino neutralized $C_{12}$-$C_{20}$ alkylsulfates, $C_{12}$-$C_{20}$ alkylpolyglucosides; mono- and di-substituted $C_{12}$-$C_{20}$ alkylphosphates; ethoxylated fatty alcohols preferably oleth-2, laureth-4, laureth-23, ethoxylated fatty acids such as hydrogenated castor oil ethoxylates; and natural ingredients, such as saponins or phospholipids (such as lecithin). Many commercial choices of surfactant types are available per the McCutcheons emulsifiers guide book and are acceptable herein if they are non-irritating or non-toxic to the skin and do not impart a poor skin feel. Polymeric emulsifiers like alkoxymodified polysiloxanes (such as Abil series—Degussa), ammonium polyacryloyldimethyl taurate and acrylate copolymers (Simulgel series—Seppic), may also be used.

In another preferred feature, the oil-phase of the emulsion contains one or more of the following ingredients: 1.0 to about 20% by weight of a silicone-elastomer cross-polymer gel. More specifically, the silicone elastomer gel may be selected from the group consisting of the reaction product of:
≡Si—H containing polysiloxane with the following:
an alpha, omega diene, preferably an alpha, omega vinylpolydimethicone, in the presence of a platinum catalyst and a solvent comprised of low molecular weight polysiloxane (linear-or cyclic), vegetable oils (such as jojoba or castor), paraffin, petrolatum, hydrogenated polyisobutene, and mineral oil, such that the solvent content of the silicone elastomer gel is 85-96% by weight, preferably 90-95% by weight, wherein the elastomer gel viscosity is greater than 200 cs, preferably greater than 50,000 cs to about 4,000,000 cs on the high end of viscosity and wherein the ≡Si—H containing polysiloxane of part I is represented by compounds of formula:
$SiO((CH_3)_2SiO)_a(CH_3HSiO)_bSi(CH_3)_3$ or formula
$H(CH_3)_2SiO((CH_3)_2SiO)_aSi(CH_3)_2H$ or formula
$H(CH_3)_2SiO((CH_3)_2SiO)_a(CH_3HSiO)_bSi(CH_3)_2H$ where a is 1-250 and b is 1-250;
where, the alpha, omega diene of part II is a compound of the formula $CH_2$=$CH(CH_2)_xCH$=$CH_2$, with representative examples including 1,4-pentadiene; 1,5-hexadiene; 1,6-heptadiene; 1,7-octadiene; 1,8-nonadiene; 1,9-decadiene; 1,11-dodecadiene; 1,13-tetradecadiene and 1,19-eicosadiene or the organo-silicone formula $CH_2$=$CH(CH_3)_2SiO$ $((CH_3)_2SiO)_cSi(CH_3)_2CH$=$CH_2$ where c is 1-200;
where the platinum catalyst is represented by hexachloroplatinic acid in a solvent, or a platinum (0) complex of $Pt_2\{[(CH_2$=$CH)Me_2Si]_2O\}$.

Examples of silicone elastomer gels include:
i. a cross-linked or partially cross-linked cyclomethicone (and) dimethicone crosspolymer;
ii. a cross-linked or partially cross-linked polydimethicone crosspolymer (For example INCI name polysilicone-11, more specifically Gransil GCM-5 a gel with D5 cyclomethicone as solvent, from Grant Industries, Elmwood Park N.J.);
iii. a cross-linked or partially cross-linked cyclomethicone (and) vinyldimethicone/methicone crosspolymer; or
iv. a cross-linked dimethicone/vinyldimethicone crosspolymer.

In still another feature, the oil-phase of the emulsion contains 0.01% to about 0.5% by weight of retinoic acid or ester. The preferred ester of retinoic acid is: all-trans retinoic 1-hydroxy-3,3-dimethyl-2-butanone ester (Formula 1)

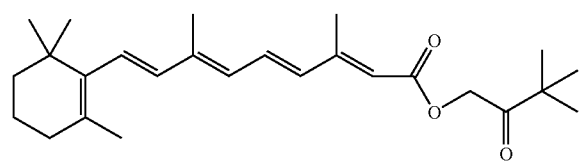

In yet another preferred feature, the aqueous phase of the emulsion contains 0.01% to about 2% by weight of a non-comedogenic, hydrated film-forming graft copolymer formed from the solution polymerization of dimethylacrylamide, acrylic acid, polystyrene, and methacrylate monomers to maintain dermal contact of the peptide emulsion for extended intervals of time. More specifically, the aqueous component of the cosmetic delivery vehicle contains 0.1% to about 2% by weight of a non-comedogenic, hydrated film-forming graft copolymer formed from the solution polymerization of dimethylacrylamide, acrylic acid, polystyrene, and methacrylate monomers having a viscosity of 50,000 to 300,000 cps at 15% solids in water. The commercial example is InvisaSkin™ (Grant Industries, Elmwood Park N.J. USA), a hydrated dimethylacrylamide/acrylic acid/polystyreneacrylate copolymer which is a liquid with a viscosity of 80,000 cps and a non-volatiles content of about 13.0 to about 17.0% by weight polymer. The aforementioned polymer was originally prepared as a non-comedogenic surgical aid for adhering skin/mucal membranes and has beneficial adhesion and hydration properties that are advantageous in long term delivery of the peptide and botanical active.

The emulsion compositions of the present invention may also include a safe and effective amount of a penetration enhancing agent. By "safe and effective amount" is meant an amount sufficient to enhance penetration of peptide and *Lycium barbarum* glycoconjugates into the skin but not so much as to cause any side effects or skin reactions, generally from about 1% to about 5% of the composition. Besides acting as peptide solvent, dimethylisosorbide and ethoxdiglycol may act as penetration enhancing agents. Examples of other useful penetration enhancers, include a penetration-enhancing vehicle consisting essentially of (a) N—(2-hydroxyethyl)-pyrrolidone and (b) a cell envelope disordering compound selected from methyl laurate, oleic acid, oleyl alcohol, mono-olein, myristyl alcohol, and mixtures thereof, wherein component (a) and (b) are present in a ratio of (a):(b) of about 1:5 to about 500:1 by weight. U.S. Pat. No. 4,557,934 teaches a pharmaceutical composition comprising the penetration enhancing agent 1-dodecylazacycloheptan-2-one, and a penetration enhancing diol or cycloketo compound selected from the group consisting of: 1,2-propanediol, 1,3-propanediol, 1,2-butanediol, pyrrolidone; 1-(2-hydroxyethyl)azacyclopentan-2-one, and mixtures thereof. U.S. Pat. No. 4,130,667 describes a penetration enhancer comprising:

(a) at least about 0.1% by weight of a sugar ester selected from sucrose monooctanoate, sucrose monodecanoate, sucrose monolaurate, sucrose monomyristate, sucrose monopalmitate, sucrose monostearate, sucrose monooleate, and sucrose dioleate; and (b) at least about 0.1% by weight of a phosphine oxide compound selected from octyl or monyl or decyl or undecyl or dodecyl-dimethyl phosphine oxide, and the 2-hydroxydecyl derivative thereof.

It is noteworthy to mention some amphiphilic penetration enhancers also function as co-emulsifier. The emulsion compositions of the invention may contain, in addition to the aforementioned components, a wide variety of additional oil-soluble materials and/or water-soluble materials conventionally used in topical compositions, at their art-established levels.

Oil-soluble materials may comprise up to about 50% of the total composition, preferably up to about 30%. The compositions of the present invention can also contain from about 2% to about 50% of at least one cosmetically acceptable emollient. Various types of emollients are known, depending on whether the emollient is in the aqueous or the oil phase of the emulsions. Some emollients listed also contribute to emulsification stability.

As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp., 32-43 (1972), incorporated herein by reference contains numerous examples of suitable materials. Examples of classes of useful emollients include the following:

1. Hydrocarbon oils and waxes. Examples include mineral oil, petrolatum, microcrystalline wax, paraffins, polyethylene, perhydrosqualene and hydrogenated polyisobutene. Also included in this group are wax esters such as beeswax, spermaceti, myristyl myristate, stearyl, stearate and the derivatives thereof such as ethoxylated sorbitol beeswax ether-esters. Further included are vegetable waxes including carnauba and candelilla waxes.

2. Volatile pqlysiloxanes (linear or cyclic), nonvolatile silicone fluids such as polydimethyl siloxanes with viscosities ranging from about 10 to about 100,000 centistokes at 25° C. methylphenyl, phenyltrimethiconepolysiloxanes, water-soluble and alcohol-soluble silicone glycol copolymers including dimethicone.

3. Triglyceride esters, for example vegetable and animal fats and oils including oils of castor, safflower, primrose, jojoba, cottonseed, corn, cod liver, palm, sesame, and soybean.

4. Acetoglyceride esters, such as acetylated monoglycerides.

5. Ethoxylated glycerides, such as ethoxylated glyceryl monostearate.

6. $C_1$ to $C_{20}$ alkyl esters of fatty acids having 10 to 20 carbon atoms such as laurates, palmitates, oleates, stearates, adipates, sebacates, and lauryl lactates.

7. Alkenyl esters of fatty acids having 10 to 20 carbon atoms. Examples include oleyl myristate, oleyl stearate, and oleyl oleate.

8. Fatty acids having 10 to 20 carbon atoms. Suitable examples include pelargonic, lauric, myristic, paimitic, stearic, isostearic, hydroxystearic, oleic, linoleic, ricinoleic, arachidic, behenic, and eruric acids.

9. Fatty alcohols having 10 to 20 carbon atoms. Lauryl, myristyl, cetyl, hexadecyl, stearyl, isostearyl, hydroxystearyl, oleyl, ricinoleyl, behenyl, and erucyl alcohols, as well as 2-octyl dodecanol, are examples of satisfactory fatty alcohols.

10. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups.

11. Ether-esters such as fatty acid esters of ethoxylated fatty alcohols.

12. Collagen, lanolin and sterol and derivative thereof, including lanolin oil, lanolin wax, lanolin alcohols, lanolin fatty acids, hydrogenated lanolin, and ethoxylated, propoxylated and acetylated derivatives thereof, and liquid and semi-solid lanolin absorption bases are illustrative of emollients derived from lanolin. Also included in this group are sterols. Cholesterol and cholesterol fatty acid esters are examples thereof.

13. Polyhydric alcohols and polyether derivatives exemplified by propylene glycol, dipropylene glycol, polypropylene glycols 2000 and 4000, polyoxyethylene polyoxypropylene glycols, glycerol, sorbitol, ethoxylated sorbitol, polyethylene glycols 200-6000, poly(ethylene oxide) homopolymers (100,000-5,000,000), polyalkylene glycols and derivatives, 1,3-butylene glycol, 1,2,6-hexanetriol, ethohexadiol USP (2-ethyl-1,3-hexanediol), $C_{15}$ to $C_{18}$ vicinal glycol, and polyoxypropylene derivatives of trimethylolpropane and the fatty esters ($C_{10}$ to $C_{20}$) thereof.

14. Phospholipids, such as lecithin and derivatives.

15. Amides such as fatty acid amides, ethoxylated fatty acid amides, solid fatty acid alkanolamides.

Particularly useful moisture retaining emollients are glycerol, hexanetriol, butanetriol, lactic acid and its salts, urea, pyrrolidone carboxylic acid and its salts, amino acids, guanidine, diglycerol and triglycerol.

Various water-soluble or dispersible solvents and materials may also be present in the compositions of this invention wherein the total water phase is from about 50% to about 85% of the total composition weight. These include water, ethanol, isopropanol, hyaluronic acid and its salts, humectants, such as glycerol, sorbitol, propylene glycol, polyethylene glycol (220-600), polypropylene glycol (425-2025), alkoxylated glucose and hexanetriol, polyvinyl alcohol, butylene glycol(s), salts, and clays such as Veegumo (magnesium aluminum silicate, R. T. Vanderbilt, Inc.); soluble proteins and polypeptides; preservatives such as the methyl, ethyl, propyl and butyl esters of hydroxybenzoic acid (Parabens-Mallinckrodt Chemical Corporation), EDTA, methylisothiazolinone and imidazolidinyl areas (Germall 115—Sutton Laboratories) phenoxyethanol (diocide—Diow) chlorophenesin; and an alkaline agent such as sodium hydroxide or potassium hydroxide to neutralize, if desired, part of the fatty acids or thickener which may be present, and botanical extracts.

A wide variety of conventional sun screening agents are suitable for use in the present invention. Segarin, et al., at Chapter VIII, Pages 189 et seq., of Cosmetics Science and Technology, disclose numerous suitable agents, the disclosure of which is incorporated herein by reference. Specific suitable sun screening agents include, for example:

p-aminobenzoic acid, its salts and derivatives, anthranilates, salicylates, cinnamic acid derivatives, dihydroxycinnamic acid derivatives, trihydroxycinnamic acid derivatives, hydrocarbons, dibenzalacetone and benzalacetophenone, naphthosulfonates, dihydroxy-naphthoic acid and its salts, o- and p-hydroxy-biphenyldisulfonates, coumarin derivatives, diazoles quinine salts, quinoline derivatives, hydroxy or methoxy substituted benzophenones, uric and vilouric acids, tannic acid and its derivatives, hydroquinone, benzophenones, and the like.

Various vitamins may also be included in the compositions of the present invention. For example, Vitamin A and derivatives thereof, Vitamin $B_2$, biotin, pantothenic acid, Vitamin D, Vitamin E and mixtures thereof may be used. If desired, anti-inflammatories can be included in the compositions of the invention to enhance photoprotection benefits, particularly from UVA. Steroidal anti-inflammatories can be represented by hydrocortisone; non-steroidal anti-inflammatories by the oxicans, salicylates, acetic acid derivatives, fenamates, propionic acid derivatives, pyrazoles, substituted phenyl compounds, 2-naphthyl containing compounds, and the natural anti-inflammatory group illustrated by aloe vera. These are more fully outlined in U.S. Pat. No. 5,487,884, the entire contents of which are incorporated herein by reference.

The composition herein can also contain conventional cosmetic adjuvants and antioxidants. Representative antioxidants include ascorbic acid, vitamin E, tocopheryl acetate, betaglucan, coenzyme Q10, butylated hydroxytoluene (BHT), superoxide dismutase and the like. Adjuvants include estradiol; progesterone; pregnanalone; coenzyme Q10; methylsolanomethane (MSM); copper peptide (copper extract); plankton extract (phytosome); glycolic acid; kojic acid; ascorbyl palmitate; all trans retinol; azaleic acid; salicylic acid; broparoestrol; estrone; adrostenedione; and androstanediols. Also included are dyes, opacifiers (e.g., titanium dioxide, zinc oxide), pigments, mica, perfumes, elastin, hydrolysates, epidermal growth factor, soybean saponins, mucopolysaccharides, *Centella asiatica*, Portulaca extract, tea tree oil, grape seed extract, ginseng, ginko biloba, green tea extract, yeast extract, allantoin, idebenone, retinyl palmitate, gamma aminobutyric acid, barium sulfate and soft focus powders, like nylon, silica, urethane and PMMA.

Controlling the pH of the composition ensures that the peptide and botanical extract are not degraded. The pH of the liquid phase is formulation dependent and preferably maintained at 4.5-8.5 and more near the skin pH balance of around 5.5. Any cosmetically or pharmaceutically acceptable pH adjusting or buffering compounds can be used. Preferred are triethanolamine, sodium hydroxide and ammonium hydroxide.

The product of the invention can be prepared using good manufacturing techniques involved in the mixing and blending of cosmetic. Preferably, organic ingredients, such as the emulsifiers, the sun screens, the emollients, stabilizers and organosoluble preservatives are emulsified in water along with any organoclay material. To this emulsion can be added the remaining ingredients and finally the pH can be adjusted to the desired level. While the compositions of the invention can be made generally in any order, it is preferred that the C12-C22 actyl oligopeptide is first solubilized in dimethylisosorbide or ethoxydiglycol prior to the addition of any remaining oil phase ingredients. Mixing conditions such as temperature are within the grasp of the skill artisan. Some or all of the ingredients for the aqueous phase can be blended and then emulsified as desired.

The following examples are for illustrative purposes only and are not intended to limit the scope of the claimed invention.

EXAMPLES

Extracellular matrix provides skin with the texture, elasticity and resilience. Active materials stimulating skin matrix are of great value for skin care health and appearance. LbGp (prepared per Phytomedicine 12 (2005) 131-137) and palmitoyl hexapeptide-6 (obtained from Helix Biomedix, Bothell, Wash.) were tested together for such matrix-rebuilding activity and surprising found to show synergy as will be delineated in the following examples.

Example 1

Collagen Assay

Normal human dermal fibroblasts (Cambrex, Walkersville, Md.) were seeded into a 96-well plate and grown to confluence. They were then challenged with several concentrations of the test samples for 4 days. The fibroblast culture-conditioned medium was harvested and tested for type I collagen by sandwich ELISA using affinity-purified antibodies. Magnesium ascorbyl phosphate (MAP) was tested along with the sample as a positive control.

| HUMAN DERMAL FIBROBLAST COLLAGEN TEST | LbGp/ (mg/ml) | palmitoyl hexapeptide-6 (mg/ml) | Type I collagen Assay | Comment |
| --- | --- | --- | --- | --- |
| Lycium barbarum extract product alone | 1.25 | — | 300 | |
| Hydrophobic peptide alone | — | 0.20 | 420 | |

-continued

| HUMAN DERMAL FIBROBLAST COLLAGEN TEST | LbGp/ (mg/ml) | palmitoyl hexapeptide-6 (mg/ml) | Type I collagen Assay | Comment |
|---|---|---|---|---|
| Experimental Blend | 1.25 | 0.20 | 500 | Synergistic/Additive effect |

Example 2

Matrix Metalloproteinase (MMP) Inhibition

Collagenase activity was measured with Enzchek kit from Molecular Probes (Invitrogen) using quenched fluorescent gelatin and human metalloproteinase 9 preparation. The release of the digested, fluorescent gelatin in the presence of different test materials was measured at excitation/emission wavelengths 485/530 nm with Millipore fluorometer. An inhibited enzyme system will have a low fluorescence reading relative to the control system.

| MMP-9 Inhibition Effect | LbGp/ mg/ml | palmitoyl hexapeptide-6 (mg/ml) | Fluorescence (arbitrary scale) Time 0 | 90 min | % Inhibited | Comment |
|---|---|---|---|---|---|---|
| Control | — | — | 0 | 24 | — | |
| Lycium barbarum extract product alone | 0.25 | — | 0 | 12 | 50 | Inhibition of MMP-9 |
| Experimental Blend | 0.25 | 0.20 | 0 | 3 | 87.5 | Synergistic Inhibition |

Example 3

Tridimensional Fibroblast Scaffolding Activity

Human dermal fibroblasts were plated in 96 well plate and test materials were added. Microphotographs of living cells and TFA-fixed & sulforhodamine B-stained cells were taken 4 days later. The tests showed synergistically improved tridimensional fibroblast scaffolding activity for the blend of LbGp/palmitoyl hexapeptide-6 compared to the control without any additive and the LbGp control at 0.25% (wt/vol).

Examples 4-5

Solubilized Acyloligopeptide Intermediate.

| Ingredient | Example 4 Control g. | Example 5 Experimental g. |
|---|---|---|
| Ethoxydiglycol | 10.0 | 10.0 |
| Palmitoylhexapeptide-6 | — | 1.0 |
| Isohexadecane (and) Ammonium Polyacryloyldimethyl Taurate | 0.5 | 0.5 |
| Deionized water | 89.5 | 88.50 |
| Total | 100.0 | 100.0 |

Ingredients were added stepwise with stirring in the order shown

Example 6

Polymeric delivery intermediate.

| Ingredient | Example 6 g. |
|---|---|
| Water | 85.00 |
| dimethylacrylamide, acrylic acid, polystyrene, acrylate copolymer[1] | 15.00 |
| Total | 100.00 |

[1]InvisaSkin ™ Polymer, Grant Industries, Elmwood Park N.J.

Polymer was homogenized in the water until it fully swelled and viscosity remained fixed

Examples 7-8

Cosmetic Intermediate

| Ingredient | Example 7 Control g. | Example 8 Experimental g. |
|---|---|---|
| Example 4 Mixture | 30.0 | — |
| Example 5 Mixture | — | 30.0 |
| Example 6 Mixture | 17.0 | 17.0 |
| Water | 41.7 | 41.2 |
| 1-3,Butylene Glycol | 10.0 | 10.0 |
| LbGp | — | 0.5 |
| Sodium Benzoate | 0.3 | 0.3 |
| Phenoxyethanol | 1.0 | 1.0 |
| Total | 100.0 | 100.0 |

Procedure: Mix together in the order shown.

Examples 9-11

Cosmetic Emulsions

| Part | Ingredient | Example 9 Control g. | Example 10 Experimental g. | Example 11 Experimental g. |
|---|---|---|---|---|
| (1) | Deionized water | 41.85 | 41.85 | 41.85 |
|  | Hydroxyethyl cellulose[3] | 0.30 | 0.30 | 0.30 |
|  | 1,3-Butylene Glycol | 7.00 | 7.00 | 7.00 |
|  | Glycerol | 3.00 | 3.00 | 3.00 |
|  | Triethanolamine | 0.15 | 0.15 | 0.15 |
|  | $C_{10-12}$ alkyl polyglucoside[4] | 0.20 | 0.20 | 0.20 |
|  | Polymethylsilsesquioxane[5] | 7.0 | 7.0 | 7.0 |
|  | Diocide[6] | 0.50 | 0.50 | 0.50 |
|  | Example 7 Mixture | 10.00 | — | — |
|  | Example 8 Mixture | — | 10.00 | 10.00 |
| (2) | Cyclomethicone and Polysilicone-11[7] | 26.65 | 26.65 | 26.50 |
|  | Laureth-4 | 0.36 | 0.36 | 0.36 |
|  | Simulgel-EG | 0.26 | 0.26 | 0.26 |
|  | 5cst polydimethlysiloxane | 2.73 | 2.73 | 2.73 |
|  | all-trans retinoic 1-hydroxy-3,3-dimethyl-2-butanone ester | — | — | 0.15 |
|  | Total | 100 | 100 | 100 |

[3]Natrosol 250M, Hercules, Wilmington De
[4]Plantaren 2000 - Cognis
[5]Gransil PSQ
[6]Diow Inc.
[7]Gransil-GCM5 Grant Industries, Elmwood Park N.J.

Procedure:

Part 1 was weighed in a 250 ml beaker and mixed at 200 RPM for 15 minutes. Part 2 was weighed in a 100 ml beaker and homogenized until smooth. Part 2 was added to Part 1 until mixed uniform to form a white viscous cosmetic cream.

Example 12-13

Periorbital Elasticity Test 10 panelists had cosmetic emulsions from examples 9 and 10 applied daily over a two-week period on the periorbital zone (eye area) in a double blind test for skin elasticity improvements. A Cutometer SEM 575 skin elasticity meter was used to measure skin elasticity at the beginning and ending time intervals. The change in elastic recovery (Ur/Ue) was determined. There was a statistically significant increase in skin elasticity ($P<0.001$). Overall, there was an 29.8% improvement in skin elasticity attributed to the Example 10 experimental emulsion as compared to the control—Example 9—emulsion.

A review of examples 1-3 and 12&13 finds the LbGp/palmitoyl hexapeptide-6 blend synergistically increased type I collagen, inhibited the activity of human MMP9 (a metalloproteinase often over expressed in pathological skin conditions, such as chronic wounds) and acted like a skin matrix scaffold for dermal fibroblasts yielding a tridimensional cell layer. These in-vitro synergistic effects were confirmed exvivo by significant skin elasticity improvement, an indicator of increase collagen production and dermal fibroblast health. Altogether, these results demonstrate the unexpected synergistic matrix-rebuilding potential of the LbGp/palmitoyl hexapeptide-6 blend.

We claim:

1. A cosmetic composition for improving the dermal fibroblast matrix comprising:
   (a) palmitoyl hexapeptide-6,
   (b) an extract of *Lycium barbarum*, wherein the palmitoyl hexapeptide-6 is present in an amount of 1 part per 6.25 parts of the extract of *Lycium barbarum*, and
   a cosmetically acceptable vehicle for (a) and (b).

2. A cosmetic composition for improving the dermal fibroblast matrix comprising:
   palmitoyl hexapeptide-6,
   (b) an extract of *Lycium barbarum*, wherein the palmitoyl hexapeptide-6 is present in an amount of 1 part per 6.25 parts of the extract of *Lycium barbarum*,
   (c) a cosmetically acceptable vehicle for (a) and (b), wherein said cosmetically acceptable vehicle is an oil-in-water or water-in-oil emulsion containing an oil phase and an aqueous phase, wherein the oil phase contains (a), and 1% to 78% by weight of polysilicone-11 as a silicone-elastomer crosspolymer gel, and the aqueous phase contains (b) and 0.01% to about 2% by weight of a film-forming graft copolymer formed from the solution polymerization of dimethylacrylamide, acrylic acid, polystyrene, and methacrylate monomers, and
   (d) about 0.2% to about 5% in total of an emulsifier used to stabilize the emulsion.

3. A method of cosmetically treating the skin of a human subject which comprises the step of topically applying to the skin a cosmetically effective amount of the cosmetic composition defined in claim 1.

4. A method of cosmetically treating the skin of a human subject which comprises the step of topically applying to the skin a cosmetically effective amount of the cosmetic composition defined in claim 2.

* * * * *

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial
<220> FEATURE:
<223> OTHER INFORMATION: synthetic sequence
<220> FEATURE:
<221> NAME/KEY: MOD_RES
```

-continued

```
<222> LOCATION: (6)..(6)
<223> OTHER INFORMATION: AMIDATION
<220> FEATURE:
<221> NAME/KEY: MOD_RES
<222> LOCATION: (6)..(6)
<223> OTHER INFORMATION: AMIDATION, N-ACYLATION

<400> SEQUENCE: 1

Phe Ala Leu Leu Lys Leu
1               5

<210> SEQ ID NO 2
<211> LENGTH: 6
<212> TYPE: PRT
<213> ORGANISM: Artificial
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 2

Glu Glu Met Gln Arg Arg
1               5
```